US006994218B2

(12) United States Patent
Kawano et al.

(10) Patent No.: US 6,994,218 B2
(45) Date of Patent: Feb. 7, 2006

(54) APPARATUS FOR SORTING CELLS AND CELL ALIGNMENT SUBSTRATE OF THE SAME

(75) Inventors: Takashi Kawano, Anjo (JP); Takahiro Yamada, Gifu-ken (JP)

(73) Assignee: Aisin Seiki Kabushiki Kaisha, Kariya (JP)

( * ) Notice: Subject to any disclaimer, the term of this patent is extended or adjusted under 35 U.S.C. 154(b) by 179 days.

(21) Appl. No.: 10/400,643

(22) Filed: Mar. 28, 2003

(65) Prior Publication Data

US 2003/0209059 A1 Nov. 13, 2003

(30) Foreign Application Priority Data

Mar. 29, 2002 (JP) .............................. 2002-094877
Jan. 29, 2003 (JP) .............................. 2003-020212

(51) Int. Cl.
  *B07C 5/00* (2006.01)
(52) U.S. Cl. ........................ 209/210; 209/552; 209/644
(58) Field of Classification Search ................ 209/210, 209/552, 644, 657, 906; 422/58, 68.1, 81, 422/82; 435/4
  See application file for complete search history.

(56) References Cited

U.S. PATENT DOCUMENTS

| 3,508,655 A | * | 4/1970 | Kamentsky | .................. 210/85 |
| 3,560,754 A | * | 2/1971 | Kamentsky | .................. 209/559 |
| 3,984,307 A | * | 10/1976 | Kamentsky et al. | ........ 209/546 |
| 4,175,662 A | * | 11/1979 | Zold | ........................... 209/552 |
| 4,756,427 A | * | 7/1988 | Gohde et al. | ................ 209/3.1 |
| 5,275,787 A | * | 1/1994 | Yuguchi et al. | .......... 422/82.08 |
| 5,976,336 A | * | 11/1999 | Dubrow et al. | ............. 204/453 |
| 6,156,181 A | * | 12/2000 | Parce et al. | .................. 204/600 |
| 6,432,630 B1 | * | 8/2002 | Blankenstein | .................. 435/4 |
| 6,592,821 B1 | * | 7/2003 | Wada et al. | ............... 422/68.1 |
| 6,911,183 B1 | * | 6/2005 | Handique et al. | ........... 422/102 |
| 2003/0027225 A1 | * | 2/2003 | Wada et al. | ............... 435/7.21 |

FOREIGN PATENT DOCUMENTS

| EP | 0 545 284 | 6/1993 |
| JP | 1-235833 | 9/1989 |
| JP | 2749906 | 2/1998 |

OTHER PUBLICATIONS

Anne Y. Fu, et al., "A Microfabricated Fluorescence-activated Cell Sorter", Nature Biotechnology, vol. 17, Nov. 1999, pp. 1109-1111.

* cited by examiner

*Primary Examiner*—Donald P. Walsh
*Assistant Examiner*—Joseph C. Rodriguez
(74) *Attorney, Agent, or Firm*—Oblon, Spivak, McClelland, Maier & Neustadt, P.C.

(57) ABSTRACT

An apparatus for sorting cells includes a cell alignment portion applying a process to a cell-suspending fluid with a great number of cells and arraying the cells with a spacing between each cell, a cell information detecting portion detecting information on the cells, a cell sorting portion for sorting the cells based upon the information detected by the cell information detecting portion, a first passage of the cell alignment portion so as to let the cell-suspending fluid flow, and a second passage of the cell alignment portion, intersecting with the first passage so as to communicate therewith, letting a splitting fluid flow so as to split the flow of the cell-suspending fluid in the first passage and forming a great number of small cell-containing liquid drops.

23 Claims, 8 Drawing Sheets

FIG. 6  Known work

APPARATUS FOR SORTING CELLS AND CELL ALIGNMENT SUBSTRATE OF THE SAME

CROSS REFERENCE TO RELATED APPLICATIONS

This application is based on and claims priority under 35 U.S.C. §119 with respect to a Japanese Patent Application 2002-094877, filed on Mar. 29, 2002, and another Japanese Patent Application 2003-020212, filed on Jan. 29, 2003, the entire content of which is incorporated herein by reference.

FIELD OF THE INVENTION

This invention generally relates to an apparatus for sorting cells suspending in a cell-suspending fluid, and also a cell alignment substrate of the apparatus so as to array the cells one by one in a row.

BACKGROUND OF THE INVENTION

Conventionally, an apparatus for sorting cells has been widely utilized in the name of a flow cytometer for sorting cells suspending in a cell-suspending fluid. The apparatus for sorting the cells is provided with a cell alignment portion, which applies a process to the cell-suspending fluid, in which a great number of cells are suspended, and arrays the cells one by one in a row with a certain spacing therebetween, a cell information detecting portion, which applies a detecting process to the cells arrayed in a row by the cell alignment portion and detects information on the cells, and a cell sorting portion, which sorts the cells based upon the information detected by the cell information detecting portion.

Figure 6:
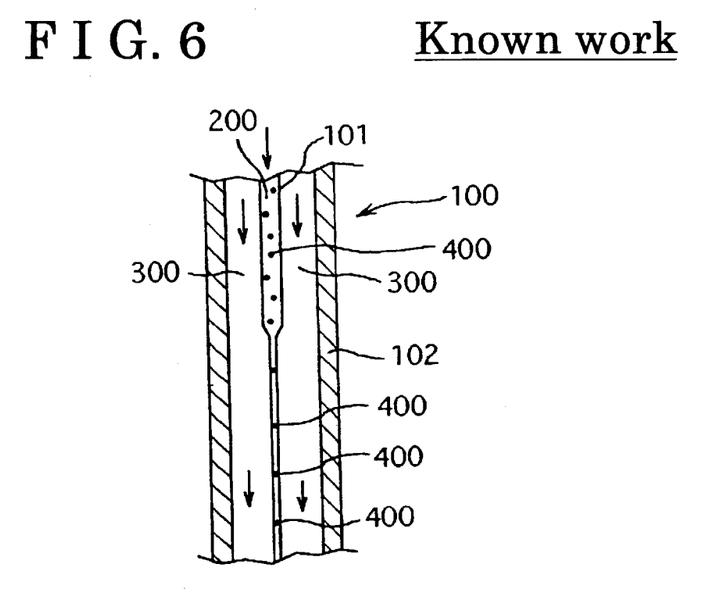
FIG. 6 is a schematic view illustrating a cell alignment portion of a known work.

As seen in FIG. 6, a cell alignment portion 100 of the above-described type of apparatus for sorting the cells has been conventionally known in the name of a sheath flow type. The cell alignment portion 100 is provided with a first nozzle 101, which possesses a cylindrical structure for letting a cell-suspending fluid 200 flow downward (in a downward direction in FIG. 6), and a second nozzle 102, which also possesses a cylindrical structure and is coaxially arranged surrounding the first nozzle 101. A sheath fluid 300 flows downward in the second nozzle 102 so as to surround the cell-suspending fluid 200 flowing downward in the first nozzle 101. The cell-suspending fluid 200 is hydrodynamically converged into a narrow flow by the sheath fluid 300, thereby the cells suspending in the cell-suspending fluid 200 is arrayed along the flow direction. In this case, a fluid passage diameter of the cell-suspending fluid 200 is narrowed corresponding to increase of a fluid pressure of the sheath fluid 300. The fluid passage diameter of the cell-suspending fluid 200 is enlarged corresponding to decrease of the fluid pressure thereof.

The above-described cell alignment portion 100 is illustrated in FIG. 11 of a Japanese Patent published as No. 2,749,906 (corresponding to a Japanese Patent Laid-Open published as No. 1991-122548). As described above, cells 400 suspending in the cell-suspending fluid 200 can be arrayed along the flow direction, thereby a cell information detecting portion (not shown) can apply an appropriate detecting process to each cell 400 and can properly detect information on each cell 400.

What is more, in the above-disclosed apparatus for sorting the cells, the flow of the cell-suspending fluid 200 is applied with supersonic vibration by an ultrasonic transducer and is converted into cell-containing liquid drops. However, the cells 400 contained in the cell-containing liquid drops, which are formed from the cell-suspending fluid 200 applied with the supersonic vibration, may be damaged. Therefore, the aforementioned method for forming the liquid drops by use of the supersonic vibration may not be recommended.

The present invention therefore seeks to provide an improved apparatus for sorting cells and a cell alignment substrate of the apparatus, by which the cells can be restrained from being damaged and a great number of cell-suspending liquid drops with a small diameter can be formed.

SUMMARY OF THE INVENTION

According to an aspect of the present invention, an apparatus for sorting cells includes a cell alignment portion applying a process to a cell-suspending fluid in which a great number of cells are suspended and arraying the cells with a spacing between each cell, a cell information detecting portion applying a detecting process to the cells arrayed by the cell alignment portion and detecting information on the cells, a cell sorting portion for sorting the cells based upon the information detected by the cell information detecting portion, a first passage included in the cell alignment portion so as to let the cell-suspending fluid flow, and a second passage included in the cell alignment portion, intersecting with the first passage so as to communicate with the first passage, letting a splitting fluid flow so as to split the flow of the cell-suspending fluid in the first passage, and forming a great number of small cell-containing liquid drops. The cell alignment portion is a common base having the first passage and the second passage.

According to another aspect of the present invention, the apparatus for sorting cells according includes a detecting position provided at the cell alignment portion, the detecting position being a position at which the cell contained in the cell-containing liquid drop arrayed by the cell alignment portion is applied with the detecting process by the cell information detecting portion, and a guiding portion for guiding the cell-containing liquid drop flowing in the second passage to the detecting position.

According to further aspect of the present invention, the apparatus for sorting cells includes a cell outlet port defined at a downstream portion of the second passage, and a gas jet portion for applying gas to the cell-containing liquid drop and for dropping the cell-containing liquid drop reached the cell outlet port out of the cell outlet port by a pressure of the gas applied to the cell-containing liquid drop.

BRIEF DESCRIPTION OF THE DRAWING FIGURES

The foregoing and additional features and characteristics of the present invention will become more apparent from the following detailed description considered with reference to the accompanying drawing figures wherein.

DETAILED DESCRIPTION OF THE INVENTION

Embodiments of the present invention will be described hereinbelow in detail with reference to the accompanying drawings.

First Embodiment

An apparatus for sorting cells according to the first embodiment of the present invention will be described hereinbelow with reference to FIGS. 1 through 4. The apparatus for sorting the cells is provided with a cell alignment substrate 1, which applies a process to a cell-suspending fluid 70 containing a great number of cells and functions as a cell alignment portion for arraying the cells one by one in a row with a certain spacing therebetween, a holding portion 10, which holds the cell alignment substrate 1, a cell information detecting portion 3, which applies a detecting process to each cell arrayed in a row by the cell alignment substrate 1 and detects information on each cell, and a cell sorting portion 5, which sorts the cells based upon the information detected by the cell information detecting portion 3.

Figure 1:
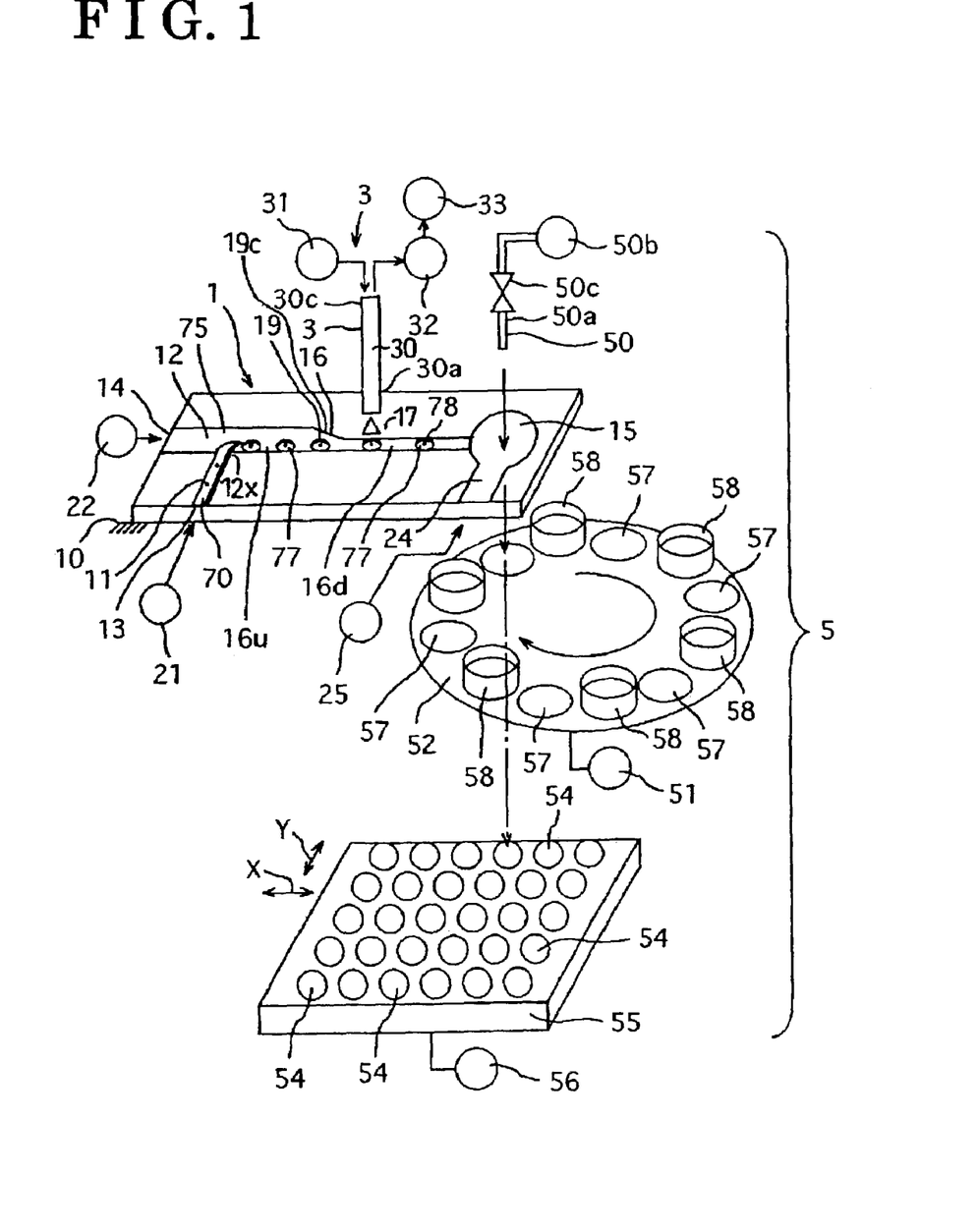
FIG. 1 is a perspective view schematically illustrating an apparatus for sorting cells according to a first embodiment of the present invention.
Figure 2:
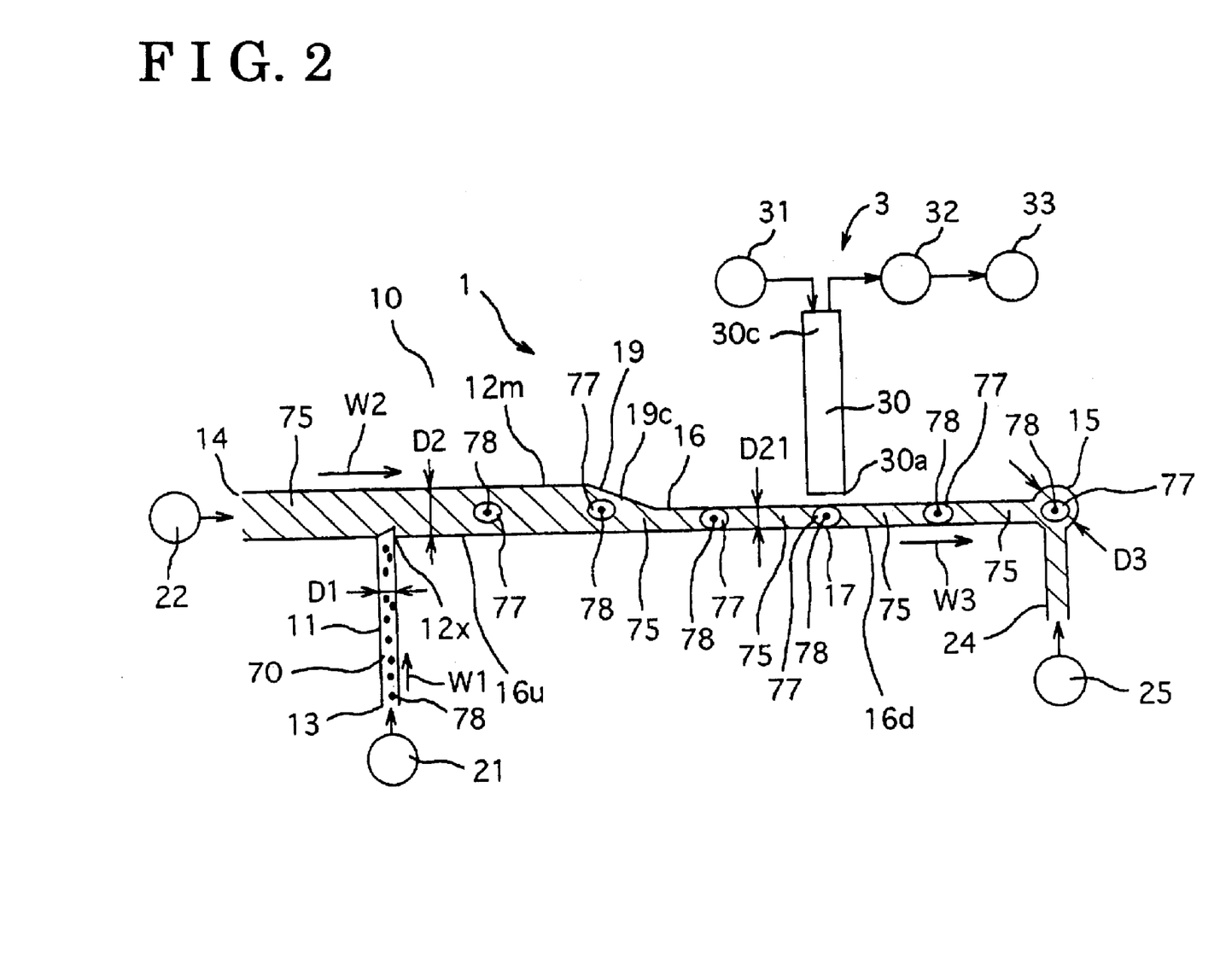
FIG. 2 is a schematic view illustrating the apparatus for sorting cells illustrated in FIG. 1 in more details.

The cell alignment substrate 1 defines a first passage 11 for letting the cell-suspending fluid 70 flow, in which a great number of cells are suspended and a second passage 12 intersecting with the first passage 11 at a T shaped angle relative to the first passage 11 and communicating therewith. The cell alignment substrate 1 is a common substrate (i.e. a common base) having the first passage 11 and the second passage 12. The cell alignment substrate 1 is horizontally arranged so that the first and second passages 11 and 12 are horizontally arranged as well. The common base as the cell alignment substrate 1 can be made of a material such as acrylate resin, a glass plate, a silicon, a metal (such as iron, aluminum, titanium and the like), and the like.

The first passage 11 is defined to possess a groove shaped structure or to be a sealed passage and straightly extends in a width direction of the cell alignment substrate 1. The first passage 11 is provided with a first inflow port 13 at an upstream side thereof. The first inflow port 13 is equipped with a first fluid source 21 having a micro pump so as to let the cell-suspending fluid 70 flow at a constant flow velocity V1. The second passage 12 is defined to possess a groove shaped structure or to be a sealed passage and straightly extends in a longitudinal direction of the cell alignment substrate 1. The second passage 12 is provided with a second inflow port 14 at an upstream side thereof, a cell outlet port 15 at a downstream side thereof, and a communicating passage 16 connecting the second inflow port 14 and the cell outlet port 15. The second inflow port 14 is equipped with a second fluid source 22 having a micro pump so as to let a splitting fluid 75 flow at a constant flow velocity V2.

The cell-suspending fluid 70 flowing in the first passage 11 includes a fluid and a great number of cells 78 contained in the fluid. The fluid represents a cell buffer solution, physiological saline, cell isotonic solution, culture solution, and the like. However, it is preferable that the fluid is not easily stuck in the passage. The cell 78 is generally hydrophilic so that the fluid of the cell-suspending fluid 70 can be hydrophilic as well. The cell 78 contained in the cell-suspending fluid 70 represents the cell, a cell constituent, a cell related substance, and organelle such as blood cell (leucocyte, erythrocyte, hematoblast, and the like), zooblast (cultured cell, isolation mechanism, and the like), a plant cell, a microbe (bacteria, Protozoa, fungi and the like), a marine life (a plankton, and the like), a sperm, a natural yeast, a mitochondria, a nucleus, a protein, nucleic acids such as DNA and RNA, an antibody, and the like. An average diameter of the cell-containing liquid drop 77 varies depending on a cell type. However, the average diameter thereof may be approximately 4 through 800 $\mu$m, especially approximately 4 through 400 $\mu$m or approximately 4 through 200 $\mu$m.

According to the first embodiment of the present invention, a passage width D2 of the second passage 12 is designed to be greater than a passage width D1 of the first passage 11. The passage width D1 of the first passage 11 and the passage width D2 of the second passage 12 are required to be sufficiently large for the cell-containing liquid drops 77 to flow therein, respectively. Although the width of each passage varies depending on a cell type, the width thereof is usually approximately 1 through 800 $\mu$m, approximately 2 through 500 $\mu$m, and approximately 5 through 300 $\mu$m. A method for forming the fist passage 11 and the second passage 12 varies depending on a material of the common substrate. The first and second passages 11 and 12 can be formed integrally with the common base being formed by use of a mold. When the common substrate is made of a material, which can be easily cut, the first and second passages 11 and 12 can be formed by applying a cutting operation to the material by use of a tool such as an end mill. On the other hand, when the common substrate is made of a material which can be etched, the first and second passages 11 and 12 can be formed by applying an etching operation to the material. Further, the first and second passages 11 and 12 can be formed by a high-energy beam.

Cell-containing liquid drops 77 are formed at an intersecting portion 12x. A diameter of the cell outlet portion 15 is designed to be greater than a diameter of the cell suspending liquid drop 77. In this case, the cell-containing liquid drop 77 can be easily dropped from the cell outlet portion 15. A passage width D21 of a downstream communicating passage 16d of the communicating passage 16 is designed to be equal to or slightly less than the diameter of the cell-containing liquid drops 77. Therefore, a liquid portion of each cell-containing liquid drop 77 is deformed by being in contact with an inner wall surface of the downstream communicating passage 16d. The passage width D21 of the downstream communicating passage 16d is designed to be constant or approximately constant over the whole-length thereof.

A detecting position 17 is preset between the second inflow port 14 of the second passage 12 and the cell outlet port 15 thereof. A cell 78 contained in each cell-containing liquid drop 77, which has been arrayed in a row by the cell alignment substrate 1, is detected at the detecting position 17 by the cell information detecting portion 3 which is assembled adjacent to the detecting position 17. The cell information detecting portion 3 detects information on each cell 78 by an optical detecting method and is provided with an optical fiber 30, of which tip end portion 30a faces at the detecting position 17 of the cell alignment substrate 1, a projecting portion 31, which possess a laser element for projecting a laser beam (a detect light) as an electromagnetic wave to the other portion 30c of the optical fiber 30 so as to electrically excite Fluorescence material in the cell 78, a light receiving portion 32, which receives the fluorescence issued from the cell 78, and a detecting portion 33, which detect information on the cell 78 based upon a signal outputted from the light receiving portion 32. According to the cell information detecting portion 3 with the above-described structure, the tip end portion 30a of the optical fiber 30 can be positioned close to the cell-containing liquid drops 77. Therefore, a main body of the cell information detecting portion 3 can be set up away from the cell alignment substrate 1. The laser beam represents argon laser, He—Ne laser, helium-cadmium laser, gallium-aluminum laser, and the like. For example, when the light receiving portion 32 receives a scattered light, the cell information detecting portion 3 detects information on the cell, such as a cell density or a cell dimension. On the other hand, when the fluorescence issued from the cell 78 is received by the light receiving portion 32, the cell information detecting portion 3 detects information on the cell, such as a cell expression and the like.

The second passage 12 is provided with a guiding portion 19 for guiding the cell-containing liquid drops 77 one by one in a row to the detecting position 17. The guiding portion 19 possesses a surface 19c (a passage width narrowing means) designed to be inclined for gradually narrowing the passage width D2 of the second passage 12 in a direction of the downstream communicating passage 16d. The guiding surface 19c is defined at a wall surface 12m opposite to a surface at a side of the first passage 11. Therefore, the guiding surface 19c according to the first embodiment of the present invention can effectively restrain the cell-containing liquid drops 77 from being displaced in a direction of the passage width D2 of the second passage 12, thereby capable of improving a detecting accuracy of the cell information.

As seen in FIG. 2, the communicating passage 16 possess not only the downstream communicating passage 16d but also an upstream communicating passage 16u. The downstream communicating passage 16d is defined at a downstream side of the guiding portion 19 and the upstream communicating passage 16u is defined at an upstream side of the guiding portion 19. The passage width D2 of the upstream communicating passage 16u is defined to possess a relatively large width and is designed to be greater than the passage width D21 of the downstream communicating passage 16d. The passage width D21 of the downstream communicating passage 16d can be a passage width for letting the cell-containing liquid drops 77 flow one by one in a row with a spacing between each liquid drop. Therefore, it is preferable that the splitting fluid 75 exists between each adjacent cell-containing liquid drop 77.

The cell sorting portion 5 is set up adjacent to the cell outlet port 15 positioned at a downstream side of the detecting position 17. The cell sorting port 5 is provided with a gas jet portion 50, a sorting plate 52 rotated by a driving portion 51 such as a motor, a collecting plate 55 (a cell collecting means) possessing a great number of collecting portions 54 for individually collecting the cells, and a driving portion 56 for moving the collecting plate 55 in an X direction and in a Y direction. The collecting plate 55 is moved by the driving portion 56 activated by a control system so as to position an intended collecting portion 54 below the cell outlet port 15.

The gas jet portion 50 is provided with a jet nozzle 50a, which faces at the cell outlet port 15 for jetting out an air (gas) to the cell-containing liquid drop 77 reached the cell outlet port 15 via the second passage 12, an air supply source (a gas supply source) 50b, which stores a compressed air, and a valve 50c, which controls an opening/closing operation of the jet nozzle 50a. The jet nozzle 50a is positioned above the cell outlet port 15. An air from the jet nozzle 50a is applied to the cell-containing liquid drop 77 reached the cell outlet port 15 in response to the opening operation of the valve 50c. Therefore, the cell-containing liquid drop 77 in the cell outlet port 15 can be dropped out of the cell outlet port 15.

The gas jetted out to the cell-containing liquid drop 77 reached the cell outlet port 15 can be an air and an inactive gas such as a nitrogen gas, an argon gas, and the like. According to the first embodiment of the present invention, the gas is jetted out to the cell-containing liquid drop 77 from the above thereof in a vertical direction. Alternatively, the gas can be jetted out thereto from the side in a lateral direction.

The cell outlet port 15 of the second passage 12 communicates with a passage 24 connected to a fluid source 25 capable of supplying a buffer solution functioning as a fluid to the cell outlet port 15 via the passage 24. Therefore, an amount of liquid portion of the cell-containing liquid drop 77 in the cell outlet port 15 is increased and the cell-containing liquid drop 77 can be upsized.

As especially seen in FIG. 1, the sorting plate 52 of the cell sorting portion 5 is positioned below the cell outlet port 15 and is provided with pass through ports 57 penetrating in a thickness direction of the sorting plate 52 and waste fluid reservoirs 58 fixed to an upper surface of the sorting plate 52. The pass through ports 57 and the waste fluid reservoirs 58 are arranged on the sampling plate 52 by turns.

When the apparatus for sorting the cells according to the first embodiment of the present invention is actually utilized, the splitting fluid 75 flows by the second fluid source 22 in an arrow direction designated with W2, i.e. from the second inflow port 14 to the cell outlet port 15, at the constant fluid velocity V2. Under the aforementioned condition, the cell-suspending fluid 70 flows by the first fluid source 21 in an arrow direction designated with W1, i.e. from the first inflow port 13 to the intersecting portion 12x, at the constant flow velocity V1. The splitting fluid 75 can be an oil possessing hydrophobic property such as a sunflower oil, an olive oil, a linseed oil, a silicon oil, a mineral oil, and the like. These described oils are highly lubricative so that the cell-containing liquid drops 77 can smoothly flow in the second passage 12.

Accordingly, the cell-suspending fluid 70 is applied with a cut force by the splitting fluid 75 flowing in the second passage 12 and is minutely cut down. Therefore, a great number of cell-containing liquid drops 77 can be consecutively formed from the cell-suspending fluid 70. The cell-containing liquid drop 77 is formed to be sufficiently large for containing a single cell therein. The cell-containing liquid drop 77 formed in the above-described manner contains a single cell or not.

The cell-containing liquid drops 77 flows with the splitting fluid 75 in a downstream direction of the second passage 12, i.e. in a direction of the detecting position 17 and the cell outlet port 15. The cell-containing liquid drops 77 flowing in the second passage 12 are regulated by the guiding portion 19 and are arrayed one by one in a row at the downstream communicating passage 16d. Therefore, the cell-containing liquid drops 77 flow along the downstream communicating passage 16d one by one in a row with an equal spacing therebetween or with an approximately equal spacing therebetween. In this case, the cell 78 contained in the cell-containing liquid drop 77 can be preferably sent to a light focus position of the cell information detecting portion 3. The laser beam as the detect light projected from the projecting portion 31 is focused on the cell 78 contained in the cell-containing liquid drop 77 via the optical fiber 30. The fluorescent material in the cell 78 is hereby electrically excited so that a light is received by the light receiving portion 32 via the optical fiber 30. Accordingly, the cell 78 at the detecting position 17 can be detected to be a target cell or not by the cell information detecting portion 3. When the cell 78 is detected to be the target cell, the control system outputs a target cell signal. On the other hand, when the cell 78 is not detected to be the target cell, the control system outputs a non-target cell signal.

The cell-containing liquid drop 77 through the detecting position 17 flows along the downstream communicating passage 16d in an arrow direction designated with W3 and is sent to the cell outlet port 15. A distance between the detecting position 17 and the cell outlet port 15 is always fixed. The fluid velocity V1 of the cell-suspending fluid 70 from the first fluid source 21 and the fluid velocity V2 of the splitting fluid 75 from the second fluid source 22 are always constant, respectively. In this case, a fluid velocity of the cell-containing liquid drop 77 can be estimated to be always constant. Therefore, the control system can comprehend a required time for the cell-containing liquid drop 77 to flow down to the cell outlet port 15 from the detecting position 17.

The buffer solution is supplied to the passage 24 by the control system when the cell-containing liquid drop 77 reaches the cell outlet port 15 or immediately prior thereto. The cell-containing liquid drop 77 in the cell outlet port 15 can be supplemented with the buffer solution and the liquid portion thereof are increased in weight. Therefore, the cell-containing liquid drop 77 can be upsized, can be prevented from being affected by surface tension thereof, and can be preferably dropped out of the cell outlet port 15.

As described above, the cell-containing liquid drop 77 is increased in weight and is then applied with the air from the nozzle 50a of the air jet portion 50 so as to be effectively dropped out of the cell outlet port 15. When the cell 78 contained in the cell-containing liquid drop 77 dropped out of the cell outlet port 15 is the target cell, the sorting plate 52 is rotated by the driving portion 51 so as to position the pass through port 57 below the cell outlet port 15. Further, the collecting plate 55 is moved by the driving portion 56 so as to position the intended collecting portion 54 below the cell outlet port 15. Therefore, the cell-containing liquid drop 77 dropped out of the cell outlet port 15 is received and collected by the intended collecting portion 54 of the collecting plate 55 via the pass through port 57 of the sorting plate 52. On the other hand, when the cell 78 contained in the cell-containing liquid drop 77 dropped out of the cell outlet port 15 is not the target cell, the sorting plate 52 is rotated by the driving portion 51 so as to position the waste fluid reservoir 58 below the cell outlet port 15. Therefore, the cell-containing liquid drop 77 dropped out of the cell outlet port 15 is received by the waste fluid reservoir 58 without passing through the pass through port 57 of the sorting plate 52.

As illustrated in FIG. 1, the pass through port 57 and the waste fluid reservoir 58 are arranged by turns so that the sorting plate 52 can be rotated at a subtle angle. Therefore, responsiveness of the sorting plate 52 can be improved with a small rotation thereof.

The cell-containing liquid drop 77 with a very small size may be greatly affected by flow resistance, friction, and surface tension. If that is the case, it is unfavorable for the cell-containing liquid drop 77 to be dropped out of the cell outlet port 15. In order to overcome the foregoing problem, the cell-containing liquid drop 77 is supplemented with the buffer solution prior to being dropped or when being dropped. Therefore, the cell-containing liquid drop 77 can be upsized so as to be easily dropped out of the cell outlet port 15.

As described above, even when the cell-containing liquid drop 77 is dropped out of the cell outlet port 15, the shock applied to the cell-containing liquid drop 77 upon being dropped can be absorbed and the cell 78 may be applied with less damage. Further, the cell 78 can be applied with less damage when the cell-containing liquid drop 77 supplemented with the buffer solution is received by the collecting portion 54 of the collecting plate 55.

Further, the guiding portion 19 of the second passage 12 according to the first embodiment of the present invention arrays the cell-containing liquid drops 77 one by one in a row in the second passage 12 and can effectively guide the cell-containing liquid drops 77 to the detecting position 17. Therefore, the cell 78 contained in the cell-containing liquid drop 77 can be properly sent to the light focus position, so that the guiding portion 19 is effective for detecting the information on the cell 78 by the cell information detecting portion 3.

Further, the spacing between each cell-containing liquid drop 77 arrayed one by one in a row can be adjusted by modifying the fluid velocity V1 of the cell-suspending fluid 70 from the first fluid source 20 and the fluid velocity V2 of the splitting fluid 75 from the second fluid source 22.

Further, the cell 78 is surrounded by the liquid portion of the cell-containing liquid drop 77 so that the cell 78 can be effectively prevented from being stuck at the second passage 12, especially at the downstream communicating passage 16d.

Figure 3A:
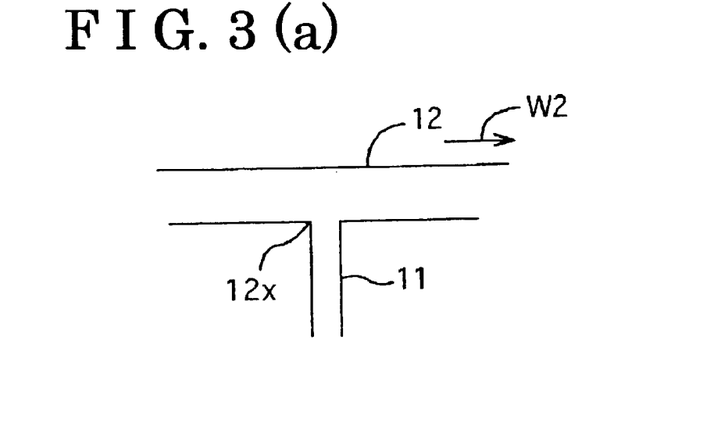
FIGS. 3(a), 3(b), and 3(c) are plan views illustrating a portion of a first passage intersecting with a second passage.
Figure 3B:
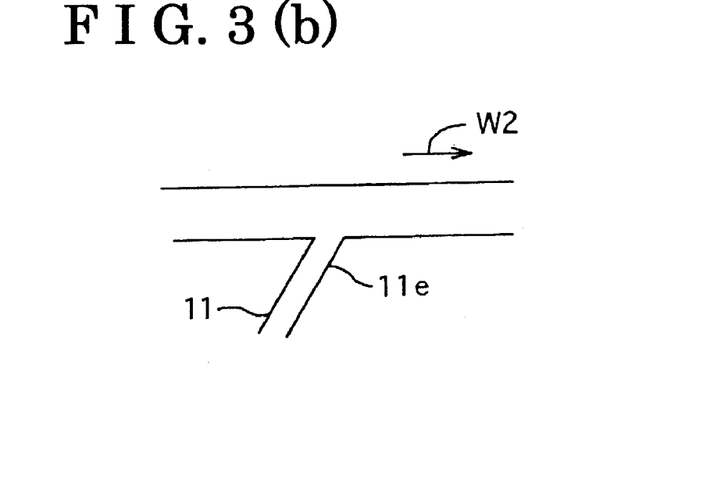
Figure 3C:
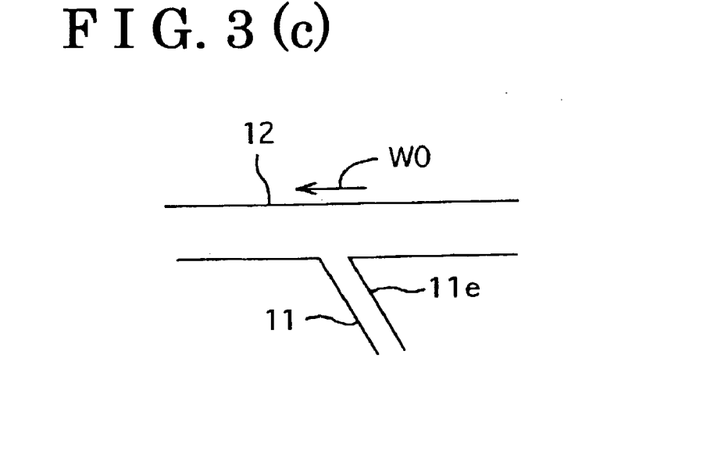
Figure 4:
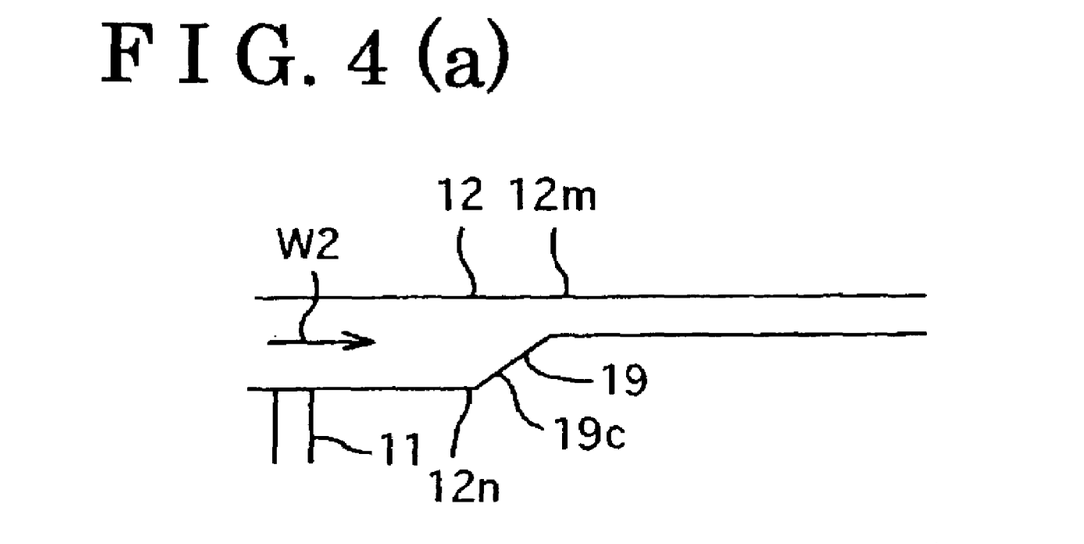
FIGS. 4(a), and 4(b) are plan views illustrating a guiding portion of the second passage.

As illustrated in FIG. 3(a), the first passage 11 intersects with the second passage 12 at the T shaped angle. Alternatively, as illustrated in FIG. 3(b), the first passage 11 can intersect with the second passage 12 with a tip end 11e reclining in the downstream direction of the second passage 12, i.e. in the arrow direction designated with W2. Further, as illustrated in FIG. 3(c), the first passage 11 can intersect with the second passage 12 with the tip end 11e reclining in the upstream direction of the second passage 12, i.e. in an arrow direction designated with W0.

As described above, the angle of the first passage 11 to be intersected with the second passage 12 is selectable as required. The first passage 11 generally intersects with the second passage 12 at ninety degrees or at an angle approximate to ninety degrees. However, the angle is not limited to the above and the first passage 11 can intersect with the second passage 12 at a T-shaped angle, with a crossed-shaped angle, or with a Y-shaped angle.

Further, as seen in FIG. 4(a), the guiding surface 19c of the second passage 12 can be defined at a wall surface 12n at the side of the first passage 11. Further, as seen in FIG. 4(b), the pair of guiding surfaces 19c of the second passage 12 can be defined at the wall surface 12m and the wall surface 12n so as to face each other.

Second Embodiment

Figure 5:
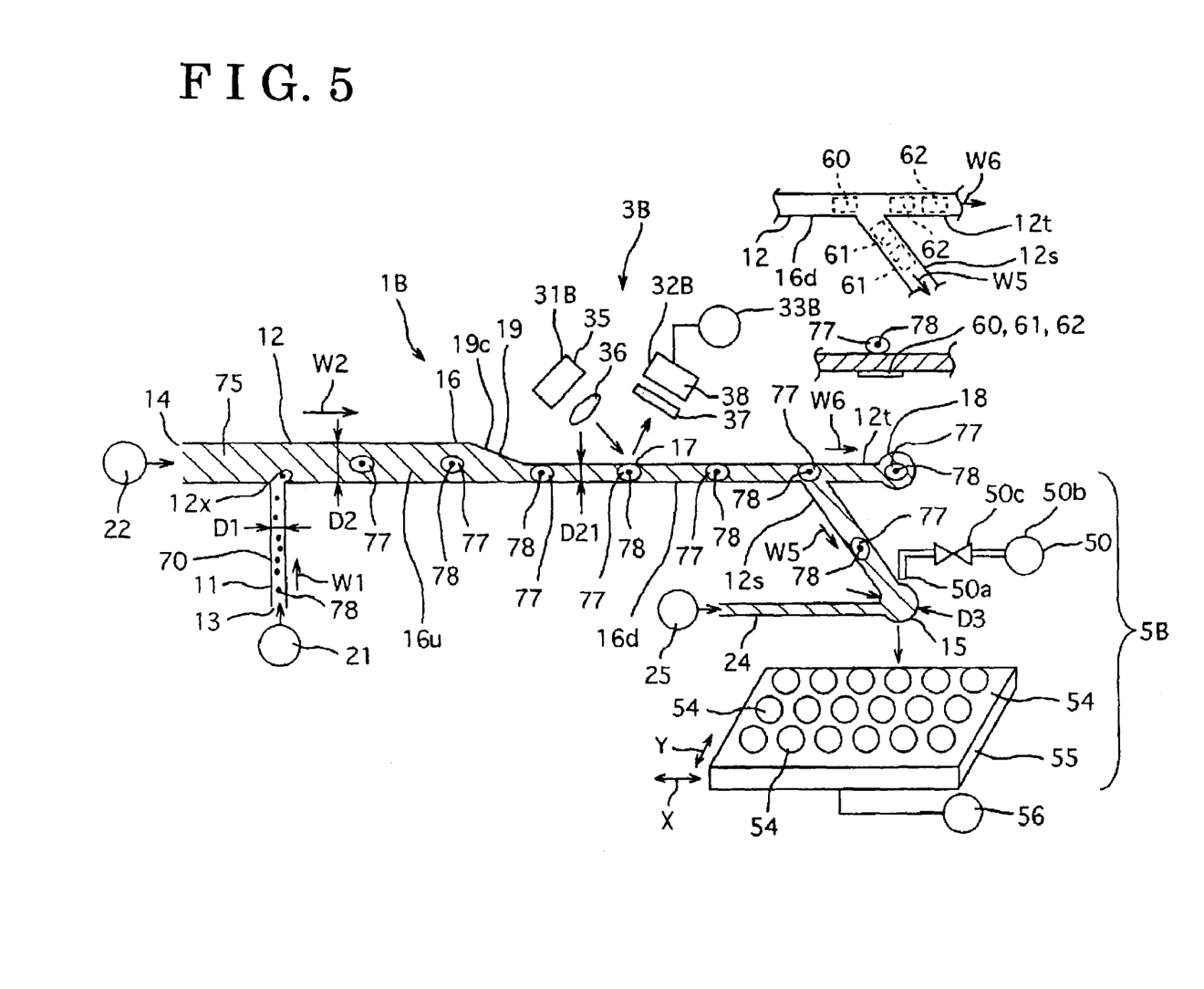
FIG. 5 is a perspective view schematically illustrating an apparatus for sorting cells according to a second embodiment of the present invention.

The apparatus for sorting cells according to the second embodiment of the present invention possess the same basic structure as the first embodiment and performs the same basic effects as the first embodiment. The apparatus for sorting cells is provided with a cell alignment substrate 1B, which applies a process to the cell-suspending fluid 70 in which a great number of cells are suspended and functions as the cell alignment portion for arraying the cells one by one in a row with a certain spacing therebetween, a holding portion (not shown), which holds the cell alignment substrate 1B, a cell information detecting portion 3B, which applies a detecting process to the cell arrayed in a row by the sell alignment substrate 1B and detects information on each cell, and a cell sorting portion 5B, which sorts the cells based upon the information detected by the cell information detecting portion 3B.

The cell alignment substrate 1B is a common substrate (i.e. a common base) having the first passage 11 for letting the cell-suspending fluid 70 with a great number of cells flow and the second passage 12 intersecting with the first passage 11 at the T shaped angle and communicating therewith. As illustrated in FIG. 5, the first passage 11 extends in the width direction of the cell alignment substrate 1B, is defined to possess the groove shaped structure or to be the sealed passage, and is provided with the first inflow port 13. The first inflow port 13 is equipped with the first fluid source 21 for letting the cell-suspending fluid 70 flow at the constant fluid velocity V1. The second passage 11 extends in the longitudinal direction of the cell alignment substrate 1B, is defined to possess the grove shaped structure or to be the sealed passage, and is provided with the second inflow port 14, the cell outlet port 15, the communicating passage 16 connecting the second inflow port 14 with the cell outlet port 15, and a cell outlet port 18. The cell outlet port 15 is employed for collecting the cell and the cell outlet port 18 is employed for disposing the liquid drop. The second inflow port 14 is equipped with the second fluid source 22 for letting the splitting fluid 75 flow at the constant fluid velocity V2.

According to the second embodiment of the present invention, the passage width D2 of the second passage 12 around the intersecting portion 12x is designed to be greater than the passage width D1 of the first passage 11. Alternatively, the passage width D2 can be designed to be less tan the passage width D1 of the first passage 11, to be approximately equal to the passage width D1, or to be equal thereto. The passage width D21 of the downstream communicating passage 16d is designed to be approximately equal to or slightly less than the diameter of the cell-containing liquid drops 77 so as to let the cell-containing liquid drops 77 flow one by one. The diameter of the cell outlet port 15 is designed to be greater than the diameter of the cell-containing liquid drop 77 generated at the intersecting portion 12x. Therefore, the cell-containing liquid drop 77 can be preferably dropped out of the cell outlet port 15.

The communicating passage 16 possesses not only the downstream communicating passage 16d but also the upstream communicating passage 16u. The downstream communicating passage 16d is defined at the downstream side of the guiding portion 19 and the upstream communicating passage 16u is defined at the upstream side thereof. The passage width D2 of the upstream communicating passage 16us is defined to possess a relatively large width and is designed to be greater than the passage width D21 of the downstream communicating passage 16d.

The detecting position 17 is defined between the second inflow port 14 of the second passage 12 and the cell outlet port 15 thereof The cell 78 contained in each cell-containing liquid drop 77, which has been arrayed in a row by the cell alignment substrate 1B, is detected at the detecting position 17 by the cell information detecting portion 3B.

The cell information detecting portion 3B is provided with a projecting portion 31B, which faces at the detecting position 17 of the cell alignment substrate 1B, a light receiving portion 32B, which receives fluorescence issued from the cell 78, and a detecting portion 33B, which detects the information on the cell 78 based upon the signal from the light receiving portion 32B. The projecting portion 31B is further provided with an LED element 35 as a light emitting element and a lens 36 condensing the light from the LED element 35. The light receiving portion 32B is formed with a filter 37 filtering a light with a specific wavelength and a light receiving element 38.

According to the second embodiment of the present invention, the guiding portion 19 is defined at the second passage 12 for guiding the cell-containing liquid drops 77 to the detecting position 17. The guiding portion 19 is defined at the upstream side of the detecting position 17 and possesses a passage of which width is reduced in a direction of the downstream of the second passage 12.

As illustrated in FIG. 5, the downstream side of the second passage 12 according to the second embodiment of the present invention branches so as to form a Y shape. That is, the downstream side of the second passage 12 branches into a collecting passage 12s connected to the cell outlet port 15 for collecting the cell 78 and a waste fluid passage 12t connected to the cell outlet port 18 (a waste fluid drain port) for disposing the liquid drop.

The cell sorting portion 5B is provided with sorting electrodes 60, 61, and 62 (a guiding means for guiding a cell-containing liquid drop), the gas jet portion 50, the collecting plate 55 (the cell collecting means) possessing a great number of collecting portions 54 for individually collecting the cells, and the driving portion 56 for moving the collecting plate 55 in an X direction or in a Y direction.

The sorting electrode 61 (a third guiding means) is provided at a back side of a bottom portion of the collecting passage 12s connected to the cell outlet port 15 for collecting the cell 78. The sorting electrode 62 (a second guiding means) is provided at a back side of a bottom portion of the waste fluid passage 12t connected to the cell outlet port 18 for disposing the liquid drop. The sorting electrode 60 (a first guiding means) is provided at a branch portion of the collecting passage 12s and the waste fluid passage 12t or at a back side of a bottom portion at an upstream side of the branch portion.

The gas jet portion 50 is provided with the jet nozzle 50a, which faces at the cell outlet port 15 for jetting out an air (gas) to the cell-containing liquid drop 77 reached the cell outlet port 15 via the second passage 12, the air supply source 50b, which stores the compressed air, and the valve 50c, which controls the opening/closing operation of the jet nozzle 50a. The jet nozzle 50a is positioned above the cell outlet port 15. An air from the jet nozzle 50a is applied to the cell-containing liquid drop 77 in the cell outlet portion 15 in response to the opening operation of the valve 50c. Therefore, the cell-containing liquid drop 77 in the cell outlet portion 15 can be preferably dropped out of the cell outlet port 15.

The cell outlet port 15 of the second passage 12 communicates with the passage 24 connected to the fluid source 25 capable of supplying the buffer solution functioning as a fluid to the cell outlet port 15 via the passage 24. Therefore, the amount of liquid portion of the cell-containing liquid drop 77 is increased and the cell-containing liquid drop 77 can be upsized.

When the apparatus for sorting cells according to the second embodiment of the present invention is actually utilized, the splitting fluid 75 flows by the second fluid source 22 in the arrow direction designated with W2, i.e. from the second inflow port 14 to the cell outlet port 15, at the constant fluid velocity V2. Under the aforementioned condition, the cell-suspending fluid 70 flows by the first fluid source 21 in the arrow direction designated with W1, i.e. from the first inflow port 13 to the intersecting portion 12x, at the constant flow velocity V1. Accordingly, the cell-suspending fluid 70 is applied with the cut force by the splitting fluid 75 flowing in the second passage 12 and is minutely cut down. Therefore, a great number of cell-containing liquid drops 77, each of which contains a single cell, can be consecutively formed from the cell-suspending fluid 70.

The cell-containing liquid drops 77 flows with the splitting fluid 75 in the downstream direction of the second passage 12, i.e. in a direction of the detecting position 17 and the cell outlet port 15. The cell-containing liquid drops 77 flowing in the second passage 12 are regulated by the guiding portion 19 and are arrayed one by one in a row at the downstream communicating passage 16d. Therefore, the cell-containing liquid drops 77 flows along the downstream communicating passage 16d one by one in a row with an equal spacing therebetween or with an approximately equal spacing therebetween. In this case, the cell 78 contained in the cell-containing liquid drop 77 can be preferably sent to the detecting position 17 of the cell information detecting portion 3B. That is, the cell 78 contained in the cell-containing liquid fluid 77 can be preferably sent to the light focus position of the cell information detecting portion 3B.

The detect light projected from the projecting portion 31B of the cell information detecting portion 3B is concentrated on the cell 78 contained in the cell-containing liquid drop 77. The fluorescent material in the cell 78 is hereby electrically excited and the electrically excited fluorescent is received by the light receiving portion 32B via the filter 37. Accordingly, the cell 78 at the detecting position 17 can be detected to be the target cell or not by the cell information detecting portion 3B. When the cell 78 is detected to be the target cell, the control system outputs the target cell signal. On the other hand, when the cell 78 is not detected to be the target cell, the control system outputs the non-target cell signal.

According to the second embodiment of the present invention, the cell-containing liquid drop 77 is electrically charged by the sorting electrode 60 disposed at the upstream of the branch portion of the waste fluid passage 12t and the collecting passage 12s.

When the cell 78 contained in the cell-containing liquid drop 77 is detected as the target cell by the cell information detecting portion 3B, the sorting electrode 61 is applied with voltage by the control system. Therefore, the cell-containing liquid drop 77 is electrostatically attracted by the sorting electrode 61, flows in a direction of the correcting passage 12s, i.e. in an arrow direction designated with W5, thereby capable of being guided to the cell outlet port 15 for collecting the cell 78. The buffer solution is supplied to the passage 24 by the control system. The cell-containing liquid drop 77 in the cell outlet port 15 can be supplemented with the buffer solution and the liquid portion thereof is increased in weight. Therefore, the cell-containing liquid drop 77 is upsized and can be preferably dropped out of the cell outlet port 15 of the second passage 12. Therefore, the sorting electrodes 60 and 61 functions as the guiding means for guiding the cell-containing liquid drops 77 containing the target cell 78 to the collecting passage 12s.

As described above, the cell-containing liquid drop 77 is increased in weight and is then applied with the air from the nozzle 50a of the air jet portion 50 so as to be effectively dropped out of the cell outlet port 15. When the cell 78 contained in the cell-containing liquid drop 77 is the target cell, the predetermined collecting portion 54 of the collecting plate 55 is positioned below the cell outlet port 15. Therefore, the cell-containing liquid drop 77 dropped out of the cell outlet port 15 is received and collected by the predetermined collecting portion 54 of the collecting portion 55. On the other hand, when the cell 78 contained in the cell-containing liquid drop 77 is not detected to be the target cell, another sorting electrode 62 is applied with voltage by the control system in substitution for the sorting electrode 61. The cell-containing liquid drop 77 is electrostatically attracted by the sorting electrode 62, flows in a direction of the waste fluid passage 12t, i.e. in an arrow direction designated with W6, thereby capable of being guided to the cell outlet port 18 for disposing the liquid drop. The cell-containing liquid drop 77 is dropped out of the cell outlet port 18 and is received by a non-illustrated waste fluid reservoir.

As described above, the sorting electrodes 60 and 62 functions as the guiding means for guiding the cell-containing liquid drop 77 to the waste fluid passage 12t when the cell 78 contained in the cell-containing liquid drop 77 is not detected to be the target cell.

The cell-containing liquid drop 77 containing the non-target cell can be dropped out of the cell outlet port 18 by itself. Alternatively, the cell-containing liquid drop 77 can be dropped out of the cell outlet port 18 by being applied with an air jet out from another gas jet portion.

Third Embodiment

The apparatus for sorting cells according to the third embodiment of the present invention possess the same basic structure as the first embodiment or the second embodiment and performs the same basic effects as the first embodiment or the second embodiment. The following description will be given only for explaining some points which are characterized only according to the third embodiment and are not characterized according to the first or second embodiment, with reference to FIGS. 7 through 9. A cell alignment substrate 1D as the cell alignment portion according to the third embodiment is provided with a substrate portion 1x, in which the first passage 11 and the second passage 12 are defined, and a cover portion 1y, which is a thin flat plate covering a surface of the substrate portion 1x so as to close the first and second passages 11 and 12. The first and second passages 11 and 12 possess cross sections of a rectangular shape, respectively. The cover portion 1y forms a surrounding wall portion 1k (illustrated in FIG. 8) surrounding the first and second passages 11 and 12 to be closed. The cover portion 1y can be adhered to the substrate portion 1x.

Figure 7:
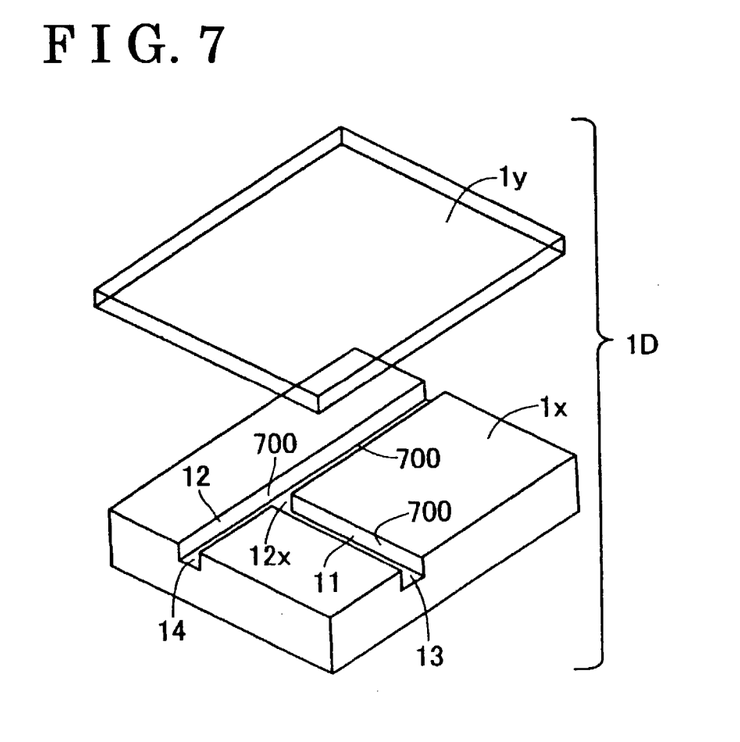
FIG. 7 is an exploded perspective view illustrating a cell alignment substrate, in which a base portion is separated from a cover portion, according to a third embodiment.
Figure 8:
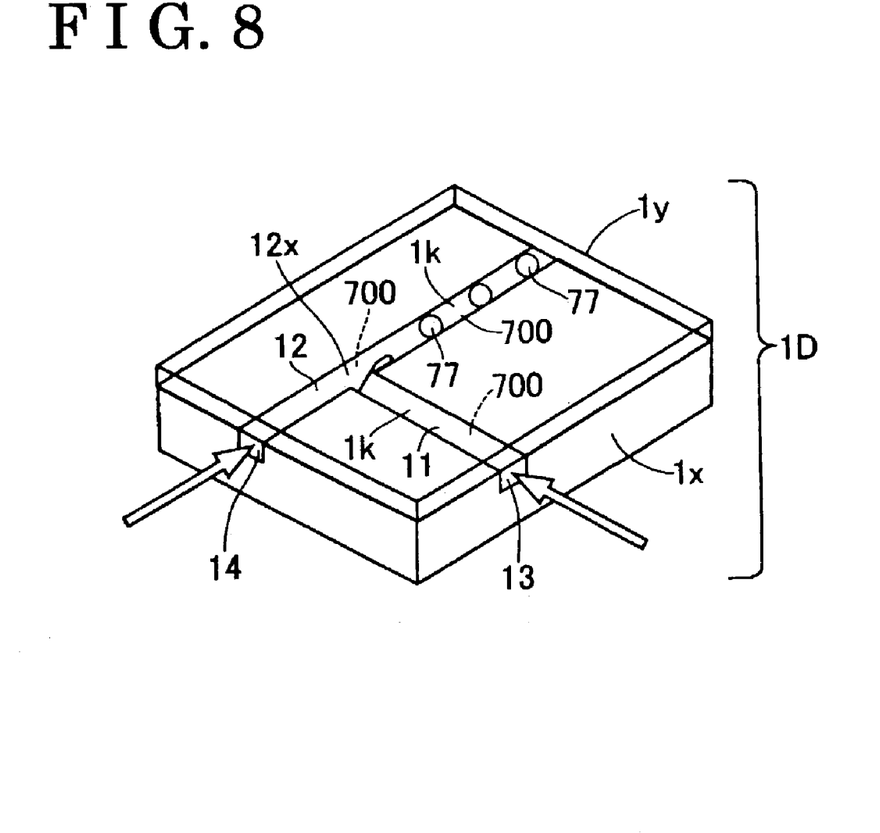
FIG. 8 is a perspective view illustrating the cell alignment substrate, in which the base portion is in contact with the cover portion, according to the third embodiment.
Figure 9:
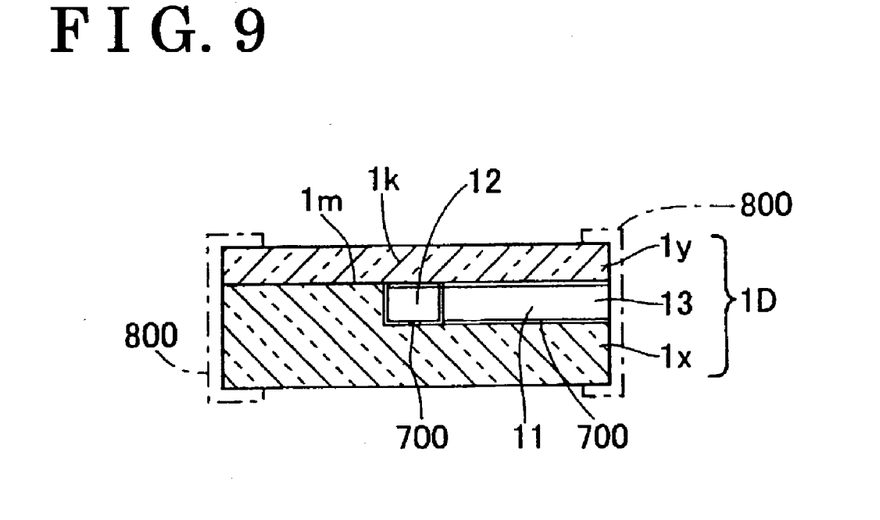
FIG. 9 is a cross sectional view of the cell alignment substrate, in which the base portion is adhered with the cover portion by a seal portion disposed between the base portion and the cover portion, according to the third embodiment.

More particularly, the cover portion 1y surrounds the first passage 11 to be closed along a cross section intersecting with the fluid flow direction of the first fluid passage 11. The cover portion 1y surrounds the second passage 12 along a cross section intersecting with the fluid flow direction of the second passage 12. Therefore, following four effects can be obtained according to the third embodiment of the present invention.
1. An area of the first passage 11 can be stabilized. An area of the second passage 12 can be stabilized.
2. The cell-suspending fluid 70 supplied to the first passage 11 can stably flow therein. The splitting fluid 75 supplied to the second passage 12 can stably flow therein.
3. A condition for forming the cell-containing liquid drops 77 can be stabilized and the number of cell-containing liquid drops 77 formed per unit time can be easily controlled.
4. The displacement of the cell-containing liquid drops 77 can be reduced or avoided when the cell information detecting portion 3 or 3B detects information on the cell arrayed one by one in a row in the cell alignment substrate 1D, thereby capable of reducing noise.

The cell information detecting portion 3 is set up at a side of the cover portion 1y. The cover portion 1y is required to be permeable for the laser beam emitted from the cell information detecting portion 3 to pass through the cover portion 1y. Therefore, the cover portion 1y and the substrate portion 1x are made of transparent acrylic resin. However, the substrate portion 1x does not necessarily have to be transparent since the substrate portion 1x is not required to be permeable.

As illustrated in FIG. 9, a membranous sealing portion 1m is disposed between the cover portion 1y and the substrate portion 1x so as to maintain the first and second passages 11 and 12 in a fluid-tight manner. In this case, each area of the first and second passages 11 and 12 can be further stabilized in response to improving the fluid-tightly closed condition thereof and fluid flowing in each passage 11 and 12 can be further stabilized as well. The sealing portion 1m can be employed with a binder for integrally adhering the cover portion 1y and the substrate portion 1x. Alternatively, a cramp member 800 can be provided for supporting the cover portion 1y and the substrate portion 1x as a single unit in substitution for the sealing portion 1m. The covering portion 1y can be detachable from the substrate portion 1x.

According to the third embodiment of the present invention, a wall surface of the first passage 11 is applied with a process so as to be lyophobic relative to the cell-suspending fluid 70. In the same manner, a wall surface of the second passage 12 is applied with a process so as to be lyophobic relative to the splitting fluid 75. For example, the lyophobic area 700 of each first and second passage 11 and 12 is coated with fluorine so as not to absorb water and oil. Therefore, the cell-suspending fluid 70 can flow more smoothly in the first passage 11 and the splitting fluid 75 can flow more smoothly in the second passage 12. In such a case, the cell 78 and the splitting fluid 75 can be restrained to be adhered to the first passage 11 and the second passage 12, respectively.

Alternatively, the lyophobic areas 700 of the first and second passages 11 and 12 can be formed by supplying lyophobic fluid to the first and second passages 11 and 12 and by drying the passages. The lyophobic fluid is in this case fluid, which do not absorb water and oil. When the cover portion 1y and the substrate portion 1x are disposable, each passage 11 and 12 is generally applied with a process for adjusting each passage to be lyophobic only one time. However, when the cover portion 1y and the substrate portion 1x can be repeatedly utilized, each passage 11 and 12 can be regularly or occasionally applied with the process.

Alternatively, the cell information detecting portion 3 can be set up at the side of the substrate portion 1x. The light is emitted from a side of the substrate portion 1x so that the substrate portion 1x is required to be permeable for the laser beam emitted from the cell information detecting portion 3 to pass through the substrate portion 1x. In this case, the cover portion 1y does not necessarily have to be transparent.

Fourth Embodiment

The apparatus for sorting cells according to the fourth embodiment of the present invention possesses the same basic structure as the first embodiment or the second embodiment and performs the same basic effects as the first embodiment or the second embodiment. The following description will be given only for explaining some points which are characterized only according to the fourth embodiment.

Figure 10:
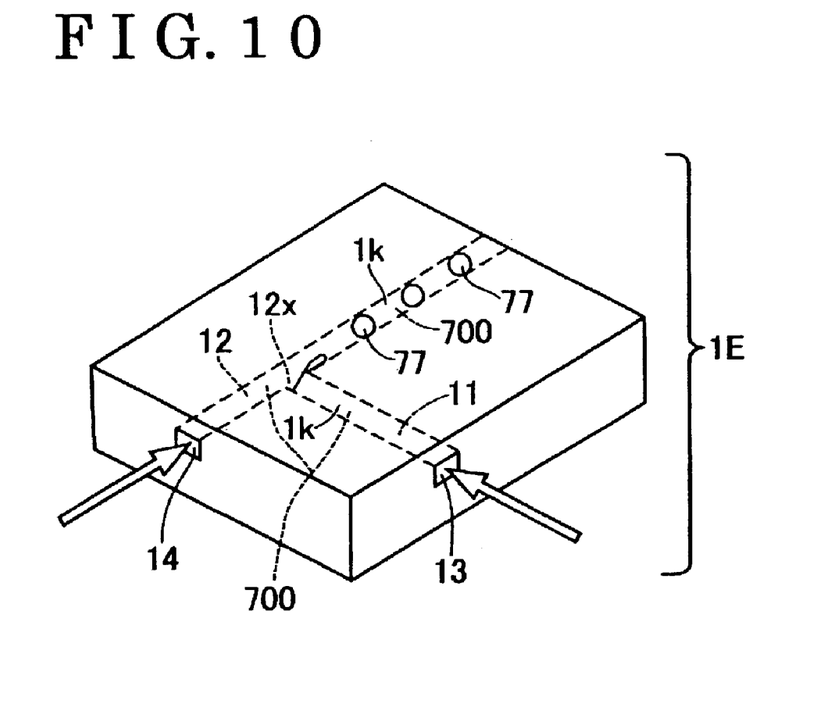
FIG. 10 is a perspective view illustrating a cell alignment substrate according to a fourth embodiment of the present invention.

A cell alignment substrate 1E functioning as the cell alignment portion possesses the first passage 11 and the second passage 12 defined inside thereof. Therefore, the surrounding wall portion 1k surrounding the first passage 11 has been already defined along a cross section intersecting with the fluid flow direction in the first passage 11. The surrounding wall portion 1k surrounding the second passage 12 has been already defined along a cross section intersecting with the fluid flow direction in the second passage 12.

The first and second passages 11 and 12 are formed with each slide core disposed in a mold. Each slide core possesses a wire shaped structure and is utilized for forming each inner space of the first passage 11 and the second passage 12. Alternatively, each passage 11 and 12 can be formed by eluting each slide core therefrom or by making a hole with laser beam irradiation thereon.

The apparatus for sorting cells according to the fourth embodiment of the present invention can perform the same effects as the third embodiment. Since the area of the second passage 12 can be stabilized, the fluid flow in the second passage 12 can be stabilized as well. Further, the condition for forming the cell-containing liquid drop 77 can be stabilized and the number of the cell-containing liquid formed per unit time can be easily controlled. The lyophobic area 700 is defined at the wall surface of the first passage 11 for adjusting the wall surface to be lyophobic relative to the cell-suspending fluid 70. The lyophobic area 700 is defined at the wall surface of the second passage 12 for adjusting the wall surface to be lyophobic relative to the splitting fluid 75.

Fifth Embodiment

The apparatus for sorting cells according to the fifth embodiment of the present invention possesses the same basic structure as the first or second embodiment and performs the same basic effects as the first or second embodiment. The following description will be given only for explaining some points which are characterized only according to the fifth embodiment.

Figure 11:
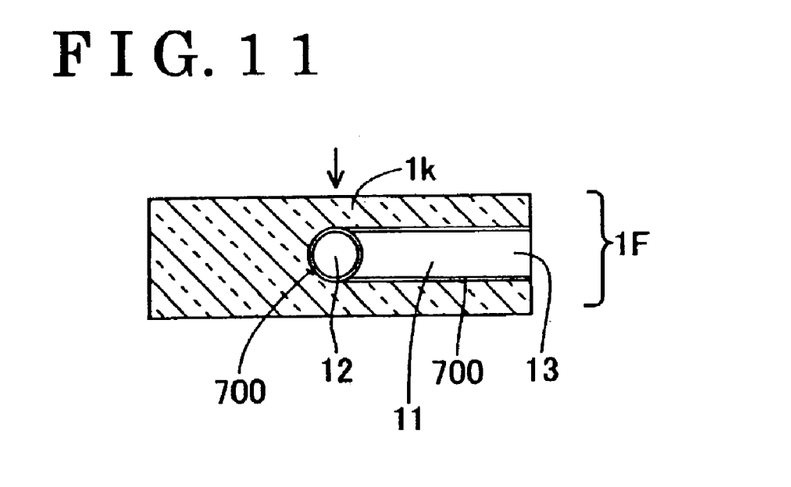
FIG. 11 is a cross sectional view illustrating a cell alignment substrate according to a fifth embodiment of the present invention.

A cell alignment substrate 1F functioning as the cell alignment portion possesses the first passage 11 and the second passage 12 defined inside thereof. Each first and second passage 11 and 12 possesses a cross section which intersects with the flow direction of each passage and is of a circular shaped structure. The circular shaped structure includes a perfect circular shape and an oval shape. The lyophobic area 700 is defined for adjusting the wall surface of the first passage 11 to be lyophobic relative to the cell-suspending fluid 70. In the same manner, the lyophobic area 700 is defined for adjusting the wall surface of the second passage 12 to be lyophobic relative to the splitting fluid 75.

According to the first and second embodiments of the present invention, the first fluid source 21 and the second fluid source 22 are the micro pumps, respectively. Alternatively, each first and second fluid source 21 and 22 can be a fluid tank or a micro cylinder device activated in response to a piston stroke. The splitting fluid 75 is not limited to the oil and can be fluorocarbon inactive fluid (Registered Trademark: Fluorinert).

According to the first embodiment of the present invention, the cell information, detecting portion 3 is provided with the optical fiber 30, of which tip end portion 30a faces at the detecting position 17 of the cell alignment substrate 1, the projecting portion 31, which possess a laser element for projecting the laser beam to the other portion 30c of the optical fiber 30, the light receiving portion 32, which receives the fluorescence, and the detecting portion 33, which detects information on the cell 78 based upon the signal outputted from the light receiving portion 32. However, the cell information detecting portion 3 is not always limited to the above-described structure.

The cell alignment substrate 1 is horizontally arranged so that the first and second passages 11 and 12 are horizontally arranged as well. Alternatively, the cell alignment substrate 1 can be vertically arranged so that the first and second passages 11 and 12 can be also vertically arranged. Further, the cell alignment substrate 1 can be arranged in a diagonally vertical direction so that the first and second passages 11 and 12 can be also arranged in the diagonally vertical direction.

According to the first and second embodiments of the present invention, the cell-containing liquid drop 77 containing a cell 78 flows in the downstream direction of the second passage 12 one by one in a row with an equal spacing therebetween. It is very preferable that a cell is contained in a liquid drop. However, the cell-containing liquid drop 77 can contain plural cells 78 therein.

The passage width D21 of the downstream communicating passage 16d is designed to be substantially equal to the diameter of the cell-containing liquid drop 77 or slightly less than that. However, the passage width D21 of the downstream communicating passage 16d can be slightly greater than the diameter of the cell-containing liquid drop 77.

According to the first and second embodiments of the present invention, the gas jet portion 50 is provided with the jet nozzle 50a, which jets out an air (gas) to the cell-containing liquid drop 77 reached the cell outlet portion 15 via the second passage 12, the air supply source 50b, which accumulates the compressed air, and the valve 50c, which controls the opening/closing operation of the jet nozzle 50a. However, the structure of the gas jet portion 50 is not always limited to the above and can be a micro pump for jetting out gas such as an air to the cell-containing liquid drop 77.

According to the second embodiment of the present invention, the sorting electrode 61 is disposed at the collecting passage 12s connected to the cell outlet port 15 for collecting the cell 78. The sorting electrode 62 is disposed at the waste fluid passage 12t connected to the cell outlet port 18 for disposing the liquid drop. The sorting electrode 60 is disposed at the branch portion between the collecting passage 12s and the waste fluid passage 12t or at the upstream side of the branch portion. However, the position of each sorting electrode 60, 61, and 62 is not limited to the above-described structure as far as each sorting electrode 60, 60, or 62 can guide the cell-containing liquid drops 77 to either the collecting passage 12s or the waste fluid passage 12t. The cell alignment substrate 1B can be fixed to the apparatus for sorting the cells or can be detachable therefrom.

The principles, preferred embodiments and mode of operation of the present invention have been described in the foregoing specification. However, the invention which is intended to be protected is not to be construed as limited to the particular embodiments disclosed. Further, the embodiments described herein is to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What we claim is:

1. An apparatus for sorting cells, comprising:
   a cell alignment portion applying a process to a cell-suspending fluid in which a great number of cells are suspended and arraying the cells with a spacing between each cell;
   a cell information detecting portion applying a detecting process to the cells arrayed by the cell alignment portion and detecting information on the cells;
   a cell sorting portion for sorting the cells based upon the information detected by the cell information detecting portion;
   a first passage included in the cell alignment portion so as to let the cell-suspending fluid flow; and
   a second passage included in the cell alignment portion, intersecting with the first passage so as to communicate with the first passage, letting a splitting fluid flow so as to split the flow of the cell-suspending fluid in the first passage, and forming a great number of small cell-containing liquid drops, the apparatus further comprising:
   a cell outlet port defined at a downstream portion of the second passage; and
   a gas jet portion for applying gas to the cell-containing liquid drop and for dropping the cell-containing liquid drop which has reached the cell outlet port out of the cell outlet port by a pressure of the gas applied to the cell-containing liquid drop.

2. The apparatus for sorting cells according to claim 1, further comprising:
   a fluid source for adding a fluid to the cell-containing liquid drop when the cell-containing liquid drop is dropped out of the cell outlet port of the second passage or prior to the dropping operation, wherein a liquid portion of the cell-containing liquid drop is increased in weight.

3. The apparatus for sorting cells according to claim 2, wherein a cell outlet port possesses a diameter being greater than a diameter of the cell-containing liquid drop.

4. An apparatus for sorting cells, comprising:
   a cell alignment portion applying a process to a cell-suspending fluid in which a great number of cells are suspended and arraying the cells with a spacing between each cell;
   a cell information detecting portion applying a detecting process to the cells arrayed by the cell alignment portion and detecting information on the cells;
   a cell sorting portion for sorting the cells based upon the information detected by the cell information detecting portion;

a first passage included in the cell alignment portion so as to let the cell-suspending fluid flow; and a second passage included in the cell alignment portion, intersecting with the first passage so as to communicate with the first passage, letting a splitting fluid flow so as to split the flow of the cell-suspending fluid in the first passage, and forming a great number of small cell-containing liquid drops, wherein at least either the first passage or the second passage is applied with a process so as to be-lyophobic relative to the cell-suspending fluid or the splitting fluid.

5. An apparatus for sorting cells, comprising:

cell alignment means for forming a number of discrete cell-containing liquid drops of a cell-suspending fluid in which a number of cells are suspended and arraying the cells with a spacing between each cell, the cell alignment means comprising a first passage for flowing a cell-suspending fluid and a second passage for flowing a splitting fluid, wherein the second passage intersects and communicates with the first passage so that the splitting fluid can split the flow of the cell-suspending fluid in the first passage;

cell information detecting means for detecting information on the cells arrayed by the cell alignment means; and cell sorting means for sorting the cells based upon the information detected by the cell information detecting means, further comprising:

a collecting passage branched from an end portion of the second passage;

a waste fluid passage branched from the end portion of the second passage, wherein the collecting passage, the waste fluid passage, and the second passage forms a Y-shaped structure;

a cell outlet port connected to the collecting passage;

a waste fluid drain port connected to the waste fluid passage;

a first guiding means disposed at an upstream portion of the branch portion of the collecting passage and the waste fluid passage so as to guide the cell-containing liquid drop to either the collecting passage or the waste fluid passage;

a second guiding means disposed at the waste fluid passage so as to guide the cell-containing liquid drop to the waste fluid drain port; and a third guiding means disposed at the collecting passage so as to guide the cell-containing liquid drop to the cell outlet port.

6. The apparatus for sorting cells according to claim 5, wherein the first guiding means is an electrode for electrically charging the cell-containing liquid drop, the second guiding means is an electrode for applying voltage to the cell-containing liquid drop electrically charged by the first guiding means when the cell information detecting means detects that the cell is not a target cell, the third guiding means is an electrode for applying voltage to the cell-containing liquid drop electrically charged by the first guiding means where the cell information detecting means detects that the cell is the target cell.

7. The apparatus, for sorting cells according to claim 6, further comprising:

a gas jet portion for applying gas to the cell-containing liquid drop in the cell outlet port and for dropping the cell-containing liquid drop in the cell outlet port out of the cell outlet port by a pressure of the gas applied to the cell-containing liquid drop.

8. An apparatus for sorting cells, comprising:

cell alignment means for forming a number of discrete cell-containing liquid drops of a cell-suspending fluid in which a number of cells are suspended and arraying the cells with a spacing between each cell, the cell alignment means comprising a first passage for flowing a cell-suspending fluid and a second passage for flowing a splitting fluid, wherein the second passage intersects and communicates with the first passage so that the splitting fluid can split the flow of the cell-suspending fluid in the first passage;

cell information detecting means for detecting information on the cells arrayed by the cell alignment means; and cell sorting means for sorting the cells based upon the information detected by the cell information detecting means, wherein one of the cell suspending fluid and the splitting fluid comprises a hydrophilic fluid and the other of the cell suspending fluid and the splitting fluid comprises a hydrophobic fluid.

9. The apparatus for sorting cells according to claim 8, wherein the cell alignment means further comprises a common base having the first passage and the second passage.

10. The apparatus for sorting cells according to claim 8, further comprising:

a detecting position provided at the cell alignment means, the detecting position being a position at which the cell contained in the cell-containing liquid drop arrayed by the cell alignment means is applied with a detecting process by the cell information detecting means; and a guiding portion for guiding the cell-containing liquid drop flowing in the second passage to the detecting position.

11. The apparatus for sorting cells according to claim 10, further comprising:

a cell outlet port defined at a downstream portion of the second passage; and a gas jet portion for applying gas to the cell-containing liquid drop and for dropping the cell-containing liquid drop which has reached the cell outlet port out of the cell outlet port by a pressure of the gas applied to the cell-containing liquid drop.

12. The apparatus for sorting cells according to claim 11, further comprising:

a fluid source for adding a fluid to the cell-containing liquid drop when the cell-containing liquid drop is dropped out of the cell outlet port of the second passage or prior to the dropping operation, wherein a liquid portion of the cell-containing liquid drop is increased in weight.

13. The apparatus for sorting cells according to claim 10, wherein the guiding portion includes a passage width narrowing means for narrowing a width of the second passage.

14. The apparatus for sorting cells according to claim 13, wherein the passage width narrowing means is an inclined surface of the second passage.

15. The apparatus for sorting cells according to claim 14, wherein the inclined surface is provided at one side of the second passage, and the one side is defined at an opposite side of the intersecting point with the first passage relative to a longitudinal direction of the second passage.

16. The apparatus for sorting cells according to claim 14, wherein the inclined surface is provided at both sides of the second passage, one of the sides is defined at an opposite side of the intersecting point with the first passage relative to a longitudinal direction of the second passage, and the other one of the sides is defined at the same side of the intersecting point with the first passage relative to the longitudinal direction of the second passage.

17. The apparatus for sorting cells according to claim 14, wherein the second passage includes an upstream communicating passage and a downstream communicating passage, the narrowing means is defined between the upstream communicating passage and the downstream communicating passage, and a diameter of the downstream communicating passage is substantially equal to or slightly less than a diameter of the cell-containing liquid drop.

18. The apparatus for sorting cells according to claim 8, wherein the cell alignment portion includes a surrounding wall portion along a cross section intersecting with a fluid flow direction in the first passage so as to surround the first passage, and another surrounding wall portion along a cross section intersecting with a fluid flow direction in the second passage so as to surround the second passage.

19. The apparatus for sorting cells according to claim 18, wherein the cell alignment portion includes a substrate portion and a cover portion, the substrate portion possesses the first passage and the second passage, and the cover portion is in contact with the substrate portion so as to cover the first passage and the second passage.

20. The apparatus for sorting cells according to claim 8, wherein the first passage intersects with the second passage at a T-shaped angle and communicates with the second passage.

21. The apparatus for sorting cells according to claim 8, wherein the second passage intersects with the first passage having a tip end at an intersecting side, the tip end possesses a slope in a downstream direction of the second passage.

22. The apparatus for sorting cells according to claim 8, wherein the second passage intersects with the first passage having a tip end at an intersecting side, and the tip end possesses a slope in an upstream direction of the second passage.

23. The apparatus for sorting cells according to claim 8, wherein the cell suspending fluid comprises a hydrophilic fluid and the splitting fluid comprises a hydrophobic fluid.

* * * * *